United States Patent
Reksohadiprodjo et al.

(10) Patent No.: US 6,777,447 B2
(45) Date of Patent: Aug. 17, 2004

(54) DERIVATIVES OF BENZYLIDENE CYCLOHEXANONE, BENZYLIDENE CYCLOPENTANONE, AND BENZYLIDENE ACETONE, AND THERAPEUTIC USES THEREOF

(76) Inventors: Mochammad Samhoedi Reksohadiprodjo, Faculty of Pharmacy, The University of Gadjah Mada, Jl. Sekip Utara, Yogyakarta (ID); Henk Timmerman, Faculty of Pharmacy, The University of Gadjah Mada, Jl. Sekip Utara, Yogyakarta (ID); Sardjiman, Faculty of Pharmacy, The University of Gadjah Mada, Jl. Sekip Utara, Yogyakarta (ID); Supardjan Amir Margono, Faculty of Pharmacy, The University of Gadjah Mada, Jl. Sekip Utara, Yogyakarta (ID); Sudibyo Martono, Faculty of Pharmacy, The University of Gadjah Mada, Jl. Sekip Utara, Yogyakarta (ID); Sugiyanto, Faculty of Pharmacy, The University of Gadjah Mada, Jl. Sekip Utara, Yogyakarta (ID); Lukman Rahman Hakim, The University of Gadjah Mada, Jl. Sekip Utara, Yogyakarta (ID); Nurlaila, The University or Gadjah Mada, Jl. Sekip Utara, Yogyakarta (ID); Arief Rahman Hakim, The University of Gadjah Mada, Jl. Sekip Utara, Yogyakarta (ID); Ika Puspitasari, Faculty of Pharmacy, The University of Gadjah Mada, Jl. Sekip Utara, Yogyakarta (ID); Arief Nurrochmad, Faculty of Pharmacy, The University of Gadjah Mada, Jl. Sekip Utara, Yogyakarta (ID); Purwantiningsih, Faculty of Pharmacy, The University of Gadjah Mada, Jl. Sekip Utara, Yogyakarta (ID); Oetari, Faculty of Pharmacy, The University of Gadjah Mada, Jl. Sekip Utara, Yogyakarta (ID); Tedjo Yuwono, Faculty of Pharmacy, The University of Gadjah Mada, Jl. Sekip Utara, Yogyakarta (ID)

( * ) Notice: Subject to any disclaimer, the term of this patent is extended or adjusted under 35 U.S.C. 154(b) by 159 days.

(21) Appl. No.: 10/085,475

(22) Filed: Feb. 27, 2002

(65) Prior Publication Data

US 2003/0092772 A1 May 15, 2003

Related U.S. Application Data

(63) Continuation-in-part of application No. 09/747,585, filed on Dec. 21, 2000, now abandoned, which is a continuation of application No. 09/026,624, filed on Feb. 20, 1998, now Pat. No. 6,541,672.

(30) Foreign Application Priority Data

Feb. 20, 1997 (ID) .............................. P 970482

(51) Int. Cl.$^7$ ...................... A01N 35/00; C07C 49/115
(52) U.S. Cl. ...................... 514/677; 514/680; 514/681; 514/684; 568/326; 568/327; 568/330
(58) Field of Search ............................... 514/677, 680, 514/681, 684; 568/326, 327, 330

(56) References Cited

U.S. PATENT DOCUMENTS 5,691,320 A * 11/1997 von Borstel et al.
6,462,075 B1 * 10/2002 Bowen et al.
6,541,672 B1 * 4/2003 Sardjiman et al.

* cited by examiner

Primary Examiner—Samuel Barts
Assistant Examiner—Sikarl A. Witherspoon
(74) Attorney, Agent, or Firm—Lahive & Cockfield, LLP; Giulio A. DeConti, Jr.; Cynthia M. Soroos

(57) ABSTRACT

Benzylidene cyclohexanone, cyclopentanone and acteone derivatives and therapeutic methods of using same are disclosed. The compounds are non-toxic and exhibit potent anti-inflammatory, antibacterial and antioxidation activity. Also, certain compounds of the invention inhibit glutathione S-transferase ("GST"), but do not irritate the gastrointestinal tract. Pharmaceutical compositions containing the compounds of the invention and pharmaceutically acceptable carriers are also disclosed.

59 Claims, No Drawings

DERIVATIVES OF BENZYLIDENE CYCLOHEXANONE, BENZYLIDENE CYCLOPENTANONE, AND BENZYLIDENE ACETONE, AND THERAPEUTIC USES THEREOF

RELATED APPLICATIONS

This application is a continuation-in-part of pending U.S. patent application Ser. No. 09/747,585, entitled, "Derivatives of Benzilidine Cyclohexanone, Benzilidine Cyclopentanone, and Benzilidine Acetone and their Synthesis," filed on Dec. 21, 2000 now abandoned, which is a continuation of allowed U.S. patent application Ser. No. 09/026,624, entitled "Derivatives of Benzilidine Cyclohexanone, Benzilidine Cyclopentanone, and Benzilidine Acetone and their Synthesis," filed on Feb. 20, 1998, which claims priority to Indonesian Patent Application Serial No. P-970482, filed on Feb. 20, 1997. The disclosures of all of the aforementioned patent applications are expressly incorporated herein by reference.

FIELD OF THE INVENTION

The invention relates to benzylidene derivatives, and more particularly to benzylidene cyclohexanone, benzylidene cyclopentanone, and benzylidene acetone, and derivatives thereof. The invention also relates to the biological activities of the aforementioned compounds in vivo and in vitro, pharmaceutical compositions thereof, and therapeutic methods of administration of same in animals.

BACKGROUND OF THE INVENTION

Curcumin (structure shown below) has a dual effect in oxygen radical reactions; i.e., it can act as a scavenger of hydroxyl radicals or catalyze the formation of hydroxyl radicals depending on the conditions. Curcumin inhibits in vitro lipid peroxide formations by liver homogenates of edemic mice. The inflammatory response induced experimentally in animals appears to be correlated with disturbances of the regulation of cellular oxidative processes, as is evident from the anti-inflammatory action of well-known antioxidants. There is evidence of a parallel between edema formation in mice induced by carragenan and the in vitro production of lipid peroxides in liver cells.

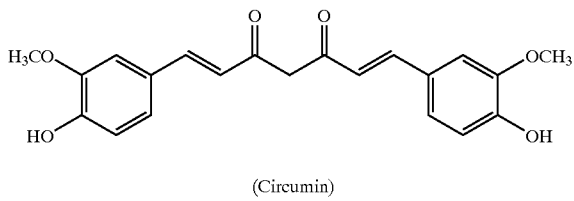

(Circumin)

Thus, curcumin has been widely used medicinally as an anti-inflammatory, anti-bacterial, antioxidant, anti-hepatotoxic, hypochlolesterolanemia, anti-cyclooxygenase, anti-cancer, and radical scavenger agent. However, it has been reported that curcumin is not stable in an alkali (pH>6.5) solution.

Toxicological studies indicate that curcumin is non-toxic at high doses. In contrast, certain pyrazolone compounds are much more toxic. For example, the use of aminophyrin as an anti-inflammatory was reported to be unsafe, because it could produce nitrosamine, a carcinogen. Dipyron, another pyrazolone derivative, is also known to give rise to adverse side effects such as agranulocytosis and allergic reaction. Similar side effects have been observed in still other by pyrazolone derivatives (phenazone, oxyphenylbutazone, phenylbutazone, etc.). The pharmacological and toxicological profile of phenylbutazone and its derivatives is illustrated below (*J. Phar. Pharmacol*, 1955, 7, 1002).

TABLE 1

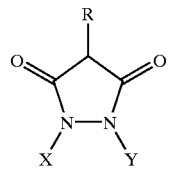

Structure of pyrazolone derivatives

| Substituent | Anti-inflammation activity (3 × 50 mg/kg) | Acute toxicity (rat), LD 50 g/kg | | |
|---|---|---|---|---|
| | | Oral | Sub-cutaneous | Intra-peritoneal |
| R = n-buthyl<br>X = Y = phenyl<br>(Phenylbutazone) | +++ | 0.73 | 0.23 | 0.23 |
| R = allyl/propyl<br>X = Y = phenyl | +++ | | ∞ | |
| R = n-butyl<br>X = Y = p-CH$_3$—C$_6$H$_4$ | +++ | | Toxicity decrease | |
| R = n-butyl<br>X = Y = p-COOH-C$_6$H$_4$ | + | ∞ | ∞ | ∞ |
| R = n-butyl<br>X = H, Y = phenyl | + | – | – | – |
| R = n-butyl<br>X = Y = (3-OH, 4-carboxy)-phenyl<br>Cyclopentanone | | | | |

SUMMARY OF THE INVENTION

The present invention is based, at least in part, on the discovery that modification of the substituents on the aromatic rings of curcumin can affect that biological activity of curcumin. In particular, substitution on the aromatic rings of curcumin with electron donating and withdrawing groups increases anti-inflammatory activity.

Also, as noted above, curcumin is unstable at a pH above 6.5. It was postulated that the instability of curcumin at pH above 6.5 may be caused by the active methylene group. Accordingly, the present invention is also based, at least in part, on the discovery that modifying curcumin by deleting the active methylene and adjacent carbonyl group yields 1,4-pentadien-3-ones that are stable at pH above 6.5 and still possess advantageous biological, e.g., antioxidative, properties.

Therefore, in one aspect, the invention is a method for treating a responsive state in a subject. The method includes administering to a subject an effective amount of a compound of formula I such that said responsive state is treated, wherein said compound of formula I is:

(I)

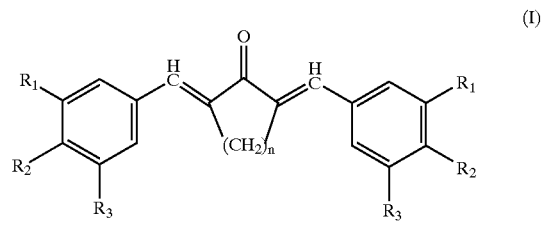

wherein n is an integer from 0 to 3, and $R_1$ and $R_2$ are each independently selected from the group consisting of methyl, ethyl, isopropyl, tertiary butyl, hydroxy, chloro, trifluoromethyl, methoxy, and dimethylamine; and $R_3$ is selected from the group consisting of methyl, ethyl, isopropyl, tertiary butyl, hydroxy, chloro, trifluoromethyl, methoxy, hydrogen, and dimethylamine; and pharmaceutically acceptable salts thereof.

In another aspect, the invention is directed to pharmaceutical compositions comprising an effective amount of a compound of formula I and a pharmaceutically acceptable carrier.

In yet another aspect, the invention is directed to certain compounds of formula I, including 2,5-bis(4-hydroxy-3,5-dimethyl benzylidene)cyclopentanone, 2,5-bis(4-hydroxy-3,5-dimethoxy benzylidene)cyclopentanone, and pharmaceutically acceptable salts thereof

DETAILED DESCRIPTION OF THE INVENTION

I. Definitions

Before further description of the invention, certain terms employed in the specification, examples and appended claims are, for convenience, collected here.

The term "alkenyl" includes unsaturated aliphatic groups analogous in length and possible substitution to the alkyls described below, but that contain at least one double bond. Unless the number of carbons is otherwise specified, "lower alkenyl" refers to an alkenyl group, as defined above, but having from two to four carbon atoms in its backbone structure.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include heteroatoms replacing one or more carbons of the hydrocarbon backbone, e.g., oxygen, nitrogen, sulfur or phosphorous atoms. In one embodiment, a straight chain or branched chain alkyl has 20 or fewer carbon atoms in its backbone (e.g., $C_1$–$C_{12}$ for straight chain, $C_3$–$C_{12}$ for branched chain). Examples of alkyl groups contemplated by the invention include, but are not limited to, methyl, ethyl, isopropyl, isobutyl, tert-butyl, branched pentyl, branched hexyl, cyclohexyl, and cyclopentyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), arylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). Unless the number of carbons is otherwise specified, "lower alkyl" refers to an alkyl group, as defined above, but having from one to three carbon atoms in its backbone structure. The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkynyl" includes unsaturated aliphatic groups analogous in length and possible substitution to the alkyls described above, but that contain at least one triple bond. Unless the number of carbons is otherwise specified, "lower alkynyl" refers to an alkynyl group, as defined above, but having from two to four carbon atoms in its backbone structure.

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). The term "aralkyl" includes alkyl groups substituted with at least one aryl group and aryl groups substituted with at least one alkyl group.

The term "bacterial disorder" includes diseases and disorder characterized by the presence of pathogenic gram-positive and gram-negative bacteria such as, for example, *S. aureus, B. subtilis, C. albicans, S. epidermidis, S. pneumoniae, S. pyogenes, E. faecalis, E faecium, Moraxella catarrhalis* and *H. influenzae*. Other examples of bacterial disorders include pneumonia, upper and lower respiratory tract infections, skin and soft tissue infections, lung infections, bone and joint infections, and other bacterial infections.

The term "cancer" includes diseases characterized by unwanted cellular proliferation. Examples of such disorders include, but are not limited to, primary and metastatic solid tumors and carcinomas of the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, hematopoietic malignancies including leukemias and chloromas, plasmacytomas, mycosis fungoides, cutaneous T-cell lymphoma/leukemia, and lymphomas including Hodgkin's and non-Hodgkin's lymphomas.

The language "chemotherapeutic agent" includes chemical agents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202–1263 (1990)), and are typically used to treat neoplastic diseases. Examples of chemotherapeutic agents include, but are not limited to: bleomycin, docetaxel (Taxotere), doxorubicin, edatrexate, etoposide, finasteride (Proscar), flutamide (Eulexin), gemcitabine (Gemzar), goserelin acetate (Zoladex), granisetron (Kytril), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), Triapine, vincristine, and vinorelbine tartrate (Navelbine). Other cytostatic agents include, for example, nitrogen mustards (e.g., mechlorethamine ($HN_2$), cyclophosphamide, Ifosfamide, Melphalan (L-sarcolysin), Chlorambucil, etc.); ethylenimines, methylmelamines (e.g., Hexamethylmelamine, Thiotepa, etc.); alkyl sulfonates (e.g., Busulfan, etc.), nitrosoureas (e.g., Carmustine (BCNU), Lomustine (CCNU), Semustine (methyl-CCNU), Streptozocin (streptozotocin), etc.); triazenes (e.g., Decarbazine (DTIC; dimethyltriazenoimidazolecarboxamide, etc.); alkylators (e.g., cis-diaminedichloroplatinum II (CDDP), etc.); folic acid analogs (e.g., Methotrexate (amethopterin), etc.); pyrimidine analogs (Fluorouracil ('5-fluorouracil; 5-FU); Floxuridine (fluorode-oxyuridine); FUdr; Cytarabine (cyosine arabinoside), etc.); purine analogs (e.g., Mercaptopuine (6-mercaptopurine; 6-MP); Thioguanine (6-thioguanine; TG); Pentostatin (2'-deoxycoformycin), etc.); vinca alkaloids (e.g., Vinblastin (VLB), Vincristine, etc.); topoisomerase inhibitors (e.g., Etoposide; Teniposide; Camptothecin; Topotecan; 9-amino-campotothecin CPT-11, etc.); antibiotics (e.g., Dactinomycin (actinomycin D); Adriamycin; Daunorubicin (daunomycin; rubindomycin); Doxorubicin; Bleomycin; Plicamycin (mithramycin); Mitomycin (mitomycin C); Taxol; Taxotere; etc.); enzymes (e.g., L-Asparaginase, etc.); biological response modifiers (e.g., Interfon alfa; interleukin 2, etc.); platinum coordination complexes (e.g., cis-diaminedichloroplatinum II (CDDP); Carboplatin); anthracendione (e.g., mitoxantrone, etc.); substituted ureas (e.g., hydroxyurea, etc.); adrenocorticosteroids (e.g., Prednisone); progestins (e.g., hydroxyprogesterone caproate; medroxyprogesterone acetate; megestrol acetate, etc.); estrogens (e.g., diethylstilbestrol; ethinyl estradiol, etc.); antiestrogens (e.g., tamoxifen, etc.); androgens (e.g., testosterone propionate, fluoxymesterone, etc.); antiandrogen (e.g., flutamide, etc.); gonadotropin-releasing hormone analogs (e.g., Leuprolide); adrenocortical suppressants (e.g., Mitotane (o,p'-DDD) aminoglutethimide, etc.); and methyl hydraxzine derivatives (e.g., procarbazine; (N-methylhydrazine, (MIH), etc.).

The term "cytostatic agent" includes agents that inhibit the growth of proliferating cells or tissue wherein the growth of such cells or tissues is undesirable. Preferrably, the the effectiveness of the cytostatic agent can be increased by the administeration of the cytostatic agent in combination with a compound of the invention. For example, the inhibition can be of the growth of malignant cells such as in neoplasms or benign cells such as in tissues where the growth is inappropriate. Examples of the types of agents which can be used include chemotherapeutic agents, radiation therapy treatments and associated radioactive compounds and methods, and immunotoxins.

The term "effective amount" of the compound is that amount necessary or sufficient to treat or prevent a responsive state, e.g. prevent or treat the various morphological and somatic symptoms of a responsive state. The effective amount can vary, depending on such factors as the size and weight of the subject, the type of illness, or the particular compound of the invention. For example, the choice of the compound of the invention can affect what constitutes an "effective amount". One of ordinary skill in the art would be able to study the aforementioned factors and make the determination regarding the effective amount of the compound without undue experimentation.

The term "$ED_{50}$" refers to the amount of a compound of the invention therapeutically effective for anti-inflammatory activity in 50% of the population. The $ED_{50}$ of a particular compound can be measured using the procedure described in Example 11, the Anti-Inflammatory Test. In an embodiment, compounds of the invention have an $ED_{50}$ value of 100 mg/kg body weight or less, 50 mg/kg body weight or less, 40 mg/kg body weight or less or 30 mg/kg body weight or less.

The term "fungal disorder" includes disorders which are related to the presence of fungus, e.g., in a subject Examples of fungal disorders in animals include topical fungal infections caused by, e.g., Candida, and dermatophytes such as Trichophyton, Microsporum or Epidermophyton, or in mucosal infections caused by, *Candida albicans* (e.g., oral thrush and vaginal candidiasis). The compounds of the invention may be useful for treatment of systemic fungal infections caused by, for example, *Candida albicans, Cryptococcus neoformans, Aspergillus flavus, Aspergillus fumigatus*, Coccidioides, Paracoccidioides, Histoplasma or Blastomyces. The compounds of the invention may be useful for treating fungal infections in immunocompromised patients such as patients with viral infections, e.g., AIDS, CMV, and influenza, cancer patients receiving chemotherapy or radiotherapy, transplant patients receiving anti-rejection agents, and patients that have received toxic chemicals, metals and radiation exposure. Other fungal disorders include aspergillosis, candidosis, chromomycosis, coccidiocycosis, cryptocococcosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, and sprotrichiosis in animals.

The term "$IC_{50}$" refers to the amount of compound necessary to inhibit fifty percent of oxidative activity. The $IC_{50}$ can be measured for example by the method described in Example 13 (Lipid Peroxidation Activity Test) and also by the method described by Haenen and Bast (*FEBS Letters*; 159(1–2):24–8 (1983)). In an embodiment, the $IC_{50}$ value of a compound of the invention is 5 $\mu$M or less, 4 $\mu$M or less, 3 $\mu$M or less, 2 $\mu$M or less, or, preferably, 1 $\mu$M or less.

The language "in combination with" a cytostatic agent includes co-administration of the compound of the invention and the cytostatic agent, administration of the compound of the invention first, followed by the cytostatic agent and administration of the cytostatic agent first, followed by compound of the invention.

The term "inflammatory disorders" include, for example, osteoarthritis, rheumatoid arthritis, acute and chronic infections (bacterial and fungal, including diphtheria and pertussis), acute and chronic bronchitis, sinusitis, and upper respiratory infections, including the common cold; acute and chronic gastroenteritis and colitis, acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical), and sunburn.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate,-bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The term "oxidative disorders" include disorders characterized by undesirable oxidative activity. Examples of such disorders include, but are not limited to, central nervous system disorders, Alzheimer's disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke, and injury during reperfusion procedures.

The term "responsive state" includes states which can be treated by the administration of an effective amount of a compound of the invention. Examples of responsive states include inflammatory disorders, cancer, fungal disorders, oxidative disorders and bacterial disorders.

The term "subject" includes organisms which can be treated for responsive states using the compounds of the invention. Examples of subjects include, for example, animals, e.g., mammals, such as horses, dogs, cats, rats, rabbits, bears, cows, goats, sheep, mice, and, preferably, humans. The term "subject" also includes subjects having compromised immune systems (i.e., "immunocompromised" subjects).

II. Nomenclature of Certain Embodiments of the Invention

As noted above, the present invention is based, at least in part, on the discovery that modification of the substituents on the aromatic rings of curcumin can affect that biological activity of curcumin. In addition, it was discovered that modifying curcumin by deleting the active methylene and adjacent carbonyl group yields 1,4-pentadien-3-ones that are stable at pH above 6.5 and still possess advantageous biological properties.

Thus, certain embodiments of the invention directed to derivatives of benzylidene cyclohexanone, benzylidene cyclopentanone, and benzylidene acetone are named, with reference to formula I, as follows:

Hexagamavunone ("HGV")

"Hexa" indicates that center part of structure is a six-member ring system, "gama" corresponds to Gadjah Mada, "vu" corresponds to Vrije Universiteit, and "none" indicates that the compound is a ketone.

Pentagamavunone ("PGV")

"Penta" indicates that the center part of the structure is five-member ring system, "gama" corresponds to Gadjah Mada, "vu" corresponds to Vrije Universiteit, and "none" indicates that the compound is a ketone.

Gamavutone ("GVT")

"Gama" corresponds to Gadjah Mada, "vu" corresponds to Vrije Universiteit, and "tone" indicates that the compound contains an acetone group at the center of the molecule, which is contrary with the normal mole ratio.

III. Methods and Compounds of the Invention

In an embodiment, the invention pertains to a method for treating a responsive state in a subject. The method includes administering to a subject an effective amount of a compound of formula I:

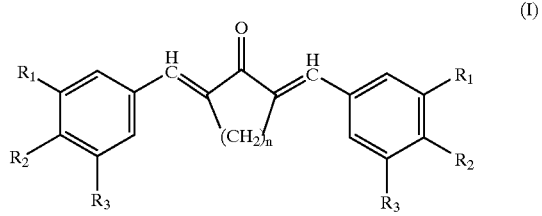

(I)

wherein n is an integer from 0 to 3, and $R_1$ and $R_2$ are each independently selected from the group consisting of methyl, ethyl, isopropyl, tertiary butyl, hydroxy, chloro, trifluoromethyl, methoxy, and dimethylamine; and $R_3$ is selected from the group consisting of methyl, ethyl, isopropyl, tertiary butyl, hydroxy, chloro, trifluoromethyl, methoxy, hydrogen, and dimethylamine; and pharmaceutically acceptable salts thereof.

Examples of responsive states include inflammatory disorders, cancer, bacterial disorders (e.g., states characterized by the presence of bacteria such as *S. Aureus, S. pneumoniae, B. subtilis*, and *C. albicans*), fungal disorders, and oxidative disorders.

In an embodiment, compounds of the invention include those in which $R_3$ is methyl, ethyl, isopropyl, tertiary butyl, hydroxy, chloro, trifluoromethyl, methoxy, or dimethylamine.

In another embodiment, n is 3 (e.g., hexagamavunone). In other embodiments, n is 2 (e.g., pentagamavunone). In a further embodiment, $R_2$ is hydroxy and at least one of R. and $R_3$ is methyl. Examples of such compounds include 2,6-bis(4-hydroxy-3,5-dimethyl benzylidene)cyclohexanone and 2,5-bis(4-hydroxy-3,5-dimethyl benzylidene) cyclopentanone. In certain embodiments, when n is 2, $R_1$ and $R_3$ are not both methyl or methoxy. In other embodiments, when n is 2 and $R_3$ is methoxy, $R^1$ is not chloro. In certain embodiments, when n is 2 or 3, $R_1$ and $R_3$ are not both tertiary butyl. In yet certain other embodiments, at least one of $R_1$, $R_2$ and $R_3$ is chloro, provided that when n is 2, $R_1$ is chloro and $R_2$ is hydroxy, then $R_3$ is not methoxy.

In another further embodiment, at least one of $R_1$ and $R_3$ is ethyl. Examples of such compounds of the invention include 2,6-bis(4-hydroxy-3,5-diethyl benzylidene) cyclohexanone and 2,5-bis(4-hydroxy-3,5-diethyl benzylidene)cyclopentanone.

In another further embodiment, at least one of $R_1$ and $R_3$ is chloro. Examples of such compounds include 2,6-bis(4-hydroxy-3,5-dichloro benzylidene)cyclohexanone and 2,5-bis(4-hydroxy-3,5-dichloro benzylidene)cyclopentanone.

In another further embodiment, at least one of $R_1$ and $R_3$ is alkoxy (e.g., methoxy). Examples of such compounds of the invention include 2,5-bis(4-hydroxy-3,5-dimethoxy benzylidene)cyclopentanone, 2,5-bis(4-hydroxy-3-methoxy benzylidene)cyclopentanone, and 2,6-bis(4-hydroxy-3,5-dimethoxy benzylidene)cyclohexanone.

In another embodiment, n is 0 (e.g, gamavutone). In an embodiment, $R_2$ is hydroxy. In a further embodiment, at least one of $R_1$ and $R_3$ is chloro. Examples of such compounds of the invention include 1,5-bis(4-hydroxy-3,5-dichloro phenyl)-1,4-pentadien-3-one. In yet another embodiment, when n is 0 or 1 and $R_2$ is hydroxy, then $R_1$ and $R_3$ are not both methoxy.

In an further embodiment, the invention pertains to a method for treating an inflammatory disorder in a subject. The method includes administering an effective amount of 2,5-bis(4-hydroxy-3-methoxybenzylidene)cyclopentanone, 2,5-bis(4-hydroxy-3,5-dimethylbenzylidene) cyclopentanone, or a pharmaceutically effective salt thereof to the subject.

In another further embodiment, the invention pertains to a method of treating cancer in a subject, by administrating a cytostatic agent in combination with a compound of the invention, such that the subject is treated for cancer. In a further embodiment, the compound of the invention is 2,5-bis(4-hydroxy-3-methoxybenzylidene)cyclopentanone, 2,5-bis(4-hydroxy-3,5-diethylbenzylidene)cyclopentanone, 2,6-bis(4-hydroxy-3,5-dimethylbenzylidene) cyclohexanone, or a pharmaceutically acceptable salt thereof.

In a further embodiment, the compounds described in Ernst et al. (DE 2009504), Chem. Ind. (London), volume 21, pp. 685–686 (1970), Borden et al., Journal of Applied Polymer Science, 22(1), 239–251 (1978), and Inayama et al. Journal of Medicinal Chemistry, 1976, Vol. 19, No. 3, pp. 433–436 are not compounds of the invention. Ernst et al. (DE 2009504), Chem. Ind. (London), volume 21, pp. 685–686 (1970), Borden et al., Journal of Applied Polymer Science, 22(1), 239–251 (1978) and Inayama et al. Journal of Medicinal Chemistry, 1976, Vol. 19, No. 3, pp. 433–436 are hereby incorporated herein by reference.

IV. Pharmaceutical Compositions

The invention also pertains, at least in part, to pharmaceutical compositions comprising an effective amount of a compound of the invention and pharmaceutically acceptable carrier. In an embodiment, the compound is of the formula I:

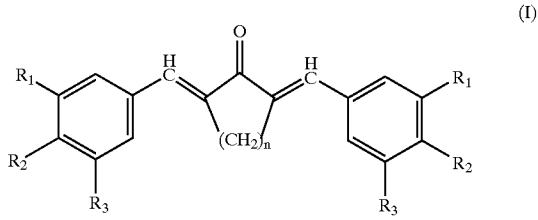

(I)

wherein n is an integer from 0 to 3, and $R_1$ and $R_2$ are each independently selected from the group consisting of methyl, ethyl, isopropyl, tertiary butyl, hydroxy, chloro, trifluoromethyl, methoxy, and dimethylamine; and $R_3$ is selected from the group consisting of methyl, ethyl, isopropyl, tertiary butyl, hydroxy, chloro, trifluoromethyl, methoxy, hydrogen, and dimethylamine; and pharmaceutically acceptable salts thereof.

In a further embodiment, the compound of the invention is 2,6-bis(4-hydroxy-3,5-dimethyl benzylidene) cyclohexanone, 2,5-bis(4-hydroxy-3,5-dimethyl benzylidene)cyclopentanone, 2,6-bis(4-hydroxy-3,5-diethyl benzylidene)cyclohexanone, 2,5-bis(4-hydroxy-3,5-diethyl benzylidene)cyclopentanone, 2,6-bis(4-hydroxy-3,5-dichloro benzylidene)cyclohexanone, 2,5-bis(4-hydroxy-3,5-dichloro benzylidene)cyclopentanone, 2,5-bis(4-hydroxy-3,5-dimethoxy benzylidene)cyclopentanone, 2,5-bis(4-hydroxy-3-methoxy benzylidene)cyclopentanone, 2,6-bis(4-hydroxy-3,5-dimethoxy benzylidene)cyclohexanone, or 1,5-bis(4-hydroxy-3,5-dichloro phenyl)-1,4-pentadien-3-one.

In a further embodiment, the effective amount is effective to treat an inflammatory disorder, bacterial disorder, cancer, oxidative disorder, or a fungal disorder. Preferably, the effective amount is not lethal to the subject.

In a further embodiment, the pharmaceutical composition for the treatment of cancer comprises a cytostatic agent in combination with the compound of the invention. Examples of compounds of the invention for the treatment of cancer include 2,5-bis(4-hydroxy-3-methoxybenzylidene) cyclopentanone, 2,6-bis(4-hydroxy-3,5-dimethylbenzylidene)cyclohexanone, and a pharmaceutically acceptable salts thereof.

In an advantageous embodiment, the invention pertains to a pharmaceutical composition comprising an effective amount for the treatment of an inflammatory disorder of 2,5-bis(4-hydroxy-3-methoxybenzylidene)cyclopentanone, 2,5-bis(4-hydroxy-3,5-dimethylbenzylidene)cyclopentanone, or a pharmaceutically effective salt thereof.

V. Preparation of Compounds of the Invention

The compounds of the invention include compounds having the general structure:

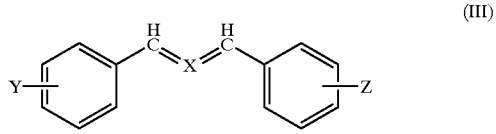

wherein:

X can be a six ring alkane derivative, a five membered ring with one carbonyl group, or aliphatic group such as acetone;

Y and Z can be various different groups: methyl, ethyl, isopropyl, tertiary butyl, hydroxy, chloro, trifluoro methyl and dimethylamine.

Advantageously, X and Y are groups with medium steric factor, positive resonance, and negative induction. Several groups are with strong negative induction. Also, most suitable bis-form is considered. Although the ratio of the aldehyde and ketone were contrary with the generally ratio, the product were always bis-form no mono product isolated in crude product. The chloro derivative (HGV-6, PGV-6, and GVT-6) in tetrahydrofuran and monosubtituted (parahydroxy derivative) are without medium in the reaction mixture. The ratio and yield were 1:1 and between 50–99% respectively.

Compounds of formula III may be prepared by aldol condensation between structures VI and V:

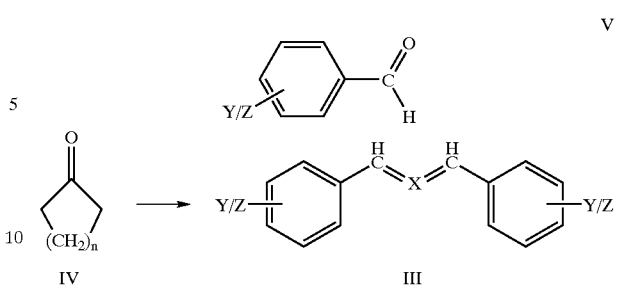

For structure III, n=0–3

The reaction between VI and V is conducted using standard procedures of chemical synthesis well known to those of ordinary skill in the art, namely aldol condensation, with or without organic solvents. The reaction utilizes suitable organic solvents such as THF, or sometimes alcohol. Acids (e.g., HCL) or bases (e.g., NaOH) may be advantageously added to the reaction mixture to accelerate the reaction process. Temperature and duration of the reaction are important factors to consider. Reaction temperatures ranging between about 0–50° C. are particularly advantageous. In an exemplary procedure, the two reactants were refluxed for several hours, and the yield of desired compound was obtained after the reaction mixture was allowed to stand for several days. The desired product was isolated by filtration, and the crude product was washed and then recrystallized. The chemical structure of the product was determined by IR, NMR and MS.

The preparation of the compounds of the inventions is exemplified in Examples 1–10 below.

VI. Biological Activity of Compounds of the Invention

The compounds of the invention were tested to determine biological activity and toxicity. In particular, the compounds were tested for antioxidative, anti-inflammatory and antibacterial activity, and for glutathione S-transferase ("GST") inhibitory activity. The compounds were also tested for acute and sub-chronic or sub-acute toxicity, and for ulcerogenicity activity.

In general, the compounds of the invention were found to possess antioxidative, anti-inflammatory and antibacterial (bacteria and fungi including C. albicans, S. aureus, and B. subtilis) activity. In addition, the compounds of the invention were found to be more stable than curcumin itself, and to be less toxic than pyrazolone derivatives.

The anti-inflammatory activity of the compounds of the invention was tested based on the inhibition of carragenin-induced swelling of rat paws. Eight compounds were found to be potent as anti-inflammatory agents using the rat paw method described in Example 11. For example, 2,5-bis(4-hydroxy-3-methoxybenzylidene)cyclopentanone and 2,5-bis(4-hydroxy-3,5-dimethylbenzylidene) cyclopentanone were found to be good antiinflammatory agents.

The antibacterial activity of the compounds of the invention was tested based on measurements of the inhibition zone during bacterial growth as described in Example 12. The bacterial growth inhibitory activity test was carried out for each of the synthesized compounds with E. coli, S. pneumoniae, B. subtilis and C. albicans. The results were measured in millimeters and compared with DMSO, nipagin and curcumin. Three compounds were found to be very potent antibacterial agents.

During the process of lipid peroxidation, poly-unsaturated membrane lipids are peroxidized in a radical reaction. The inhibitory activity of the dibenzylidene cyclohexanone and dibenzylidene cyclopentanone derivatives against in vitro microsomal lipid peroxidation was determined by the thiobarbituric acid (TBA) test (Example 13). This example used rat liver microsomes as the poly-unsaturated fatty acid (PUFA) source. It was found that compounds of the invention that contain hydroxy groups in the aromatic ring at the para position ($R_2$) are relatively active as inhibitors of lipid peroxidation. Two exceptions are 2,6-bis(4-hydroxy-3,5-dichloro benzylidene)cyclohexanone and 1,5-bis(4-hydroxy-3,5-dichloro phenyl)-1,4-pentadien-3-one.

Acute toxicity is the toxic effect level of the compounds in the animals, twenty four hours or less after single dose administration as described in Example 14. From the toxicity potency data, it was found that 2,5-bis(4-hydroxy-3-methoxy benzylidene)cyclopentanone; 2,5-bis(4-hydroxy-3,5-dimethyl benzylidene)cyclopentanone; and 2,6-bis(4-hydroxy-3,5-dimethyl benzylidene)cyclohexanone were non-toxic for male and female rats and rabbits. 2,5-bis(4-hydroxy-3-methoxy benzylidene)cyclopentanone was found to be less toxic than both 2,5-bis(4-hydroxy-3,5-dimethyl benzylidene)cyclopentanone and 2,6-bis(4-hydroxy-3,5-dimethyl benzylidene)cyclohexanone.

Ulcerogenicity level in rats was tested using the method described in Example 15. It was found that 2,5-bis(4-hydroxy-3-methoxy benzylidene)cyclopentanone; 2,5-bis(4-hydroxy-3,5-dimethyl benzylidene)cyclopentanone; and 2,6-bis(4-hydroxy-3,5-dimethyl benzylidene)cyclohexanone did not significantly adversely affect the subject as compared with the negative control (tilose 1%). When compared with acetosal (45.25 mg/kg bw) and sodium diclofenac (4.5 mg/kg bw), 2,5-bis(4-hydroxy-3-methoxy benzylidene)cyclopentanone; 2,5-bis(4-hydroxy-3,5-dimethyl benzylidene)cyclopentanone and 2,6-bis(4-hydroxy-3,5-dimethyl benzylidene)cyclohexanone resulted in less ulcerogenicity in single and multiple doses administration.

Compounds were screened for anticancer activity using the Glutathione S-transferase (GST) assay described in Example 17. It was found that 2,5-bis(4-hydroxy-3-methoxybenzylidene)cyclopentanone, 2,5-bis(4-hydroxy-3,5-diethylbenzylidene)cyclopentanone and 2,6-bis(4-hydroxy-3,5-dimethylbenzylidene)cyclohexanone had some anti-cancer activity.

VII. Exemplification of the Invention

The invention is further illustrated by the following examples which should not be construed as limiting.

Preparation of the Compounds of the Invention

EXAMPLE 1

2,6-bis(4-hydroxy-3,5-dimethylbenzylidene) cyclohexanone (HGV-1)

To 1 part of cyclohexanone and 1 part of an aldehyde were added hydrochloride acid as a catalyst and stirred at 20–50° C. for sometime, and left for several days at ambient temperature. The yield was macerated with glacial acetic acid and water, filtered, and yield was purified by crystallization with ethanol-water. Melting point 225–226° C. Yield 85%. NMR(DMSO-d6): 1.72(quintet,2H,C—$CH_2$—C); 2.24(s, 2H,—$CH_3$); 2.88(t, 4H, $H_2$C—C—$CH_2$); 7.16(s, 4H, arom); 7.52(s, 2H, —CH=); 8.78(s, 2H—OH). HRMS ($C_{24}H_{26}O_3$) obtained 362.1875; calculated 362.1882.

EXAMPLE 2

2,6-bis(4-hydroxy-3,5-diethylbenzylidene) cyclohexanone (HGV-2)

The same procedure was conducted to prepare HGV-2. Melting point 197–198° C. Yield=81%. NMR(DMSO-d6): 1.17(t, 12H—$CH_3$); 1.75(quintet, 2H, C—$CH_2$—C); 2.65(q, 8H, C—$CH_2$—Ar); 2.9(t, 4H, $H_2$C—C—$CH_2$); 7.18(s, 4H, arom); 7.56 (s, 2H, —CH=); 8.7(s, 2H, —OH). HRMS ($C_{28}H_{34}O_3$) obtained 418.2508; calculated 418.2508.

EXAMPLE 3

2,6-bis(4-hydroxy-3,5-dimethoxybenzylidene) cyclohexanone (HGV-5)

The same procedure was conducted to prepare HGV-5. Melting point 134–135° C. Yield=44%. NMR(DMSO-d6): 1.76(quintet, 2H, C—$CH_2$—C); 2.96(t, 4H, $H_2$C—C—$CH_2$); 3.83(s, 12H, —$OCH_3$); 6.86(s, 4H, arom); 7.60(s, 2H, —CH=); 8.5-9.2 (br, 2H, —OH). HRMS ($C_{24}H_{26}O_7$) obtained 426.1765; calculated 426.1678.

EXAMPLE 4

2,6-bis(4-hydroxy-3,5-dichlorobenzylidene) cyclohexanone (HGV-6)

The same procedure was conducted to prepare HGV-6. Melting point 201–202° C. Yield=43%. NMR(DMSO-d6): 1.71(quintet, 2H, C—$CH_2$—C); 2.84(t, 4H, $H_2$C—C—$CH_2$); 7.46(s, 2H, —CH=); 7.56(s, 4H, arom); 10.65(br, 2H, —OH). HRMS ($C_{20}H_{14}O_3Cl_4$) obtained 441.9699; calculated 441.9697.

EXAMPLE 5

2,5-bis(4-hydroxy-3,5-dimethylbenzylidene) cyclopentanone (PGV-1)

The same procedure was conducted to prepare PGV-1. Melting point 269–270° C. Yield=78%. NMR(DMSO-d6): 2.24(s, 12H, —$CH_3$); 3.04(s, 4H, $H_2$C—C—$CH_2$); 7.28(s, 6H, arom and —CH=); 8.92(br, 2H, —OH). HRMS ($C_{23}H_{24}O_3$) obtained 384.1729; calculated 348.1725.

EXAMPLE 6

2,5-bis(4-hydroxy-3,5-diethylbenzylidene) cyclopentanone (PGV-2)

The same procedure was conducted to prepare PGV-2. Melting point 193–194° C. Yield=92%. NMR(DMSO-d6): 1.17(t, 12H, —$CH_3$); 2.64(q, 8H, —$CH_2$—Ar); 3.03(s, 4H, $H_2$C—C—$CH_2$); 7.30(s, 4H, arom); 7.32(s, 2H, —CH=); 8.82(br, 2H, —OH). HRMS ($C_{27}H_{32}O_3$) obtained 404.2348; calculated 404.2351.

EXAMPLE 7

2,5-bis(4-hydroxy-3,5-dimethoxybenzylidene) cyclopentanone (PGV-5)

The same procedure was conducted to prepare PGV-5. Melting point 226–227° C. Yield=79%. NMR(DMSO-d6): 3.14(s, 4H, $H_2$C—$CH_2$); 3.86(s, 12H, —$OCH_3$); 7.00(s, 4H, arom); 7.40(s, 2H, —CH=); 9.12(br, 2H, —OH). HRMS ($C_{23}H_{24}O_7$) obtained 412.1519; calculated 412.1522.

EXAMPLE 8

2,5-bis(4-hydroxy-3,5-dichlorobenzylidene) cyclopentanone (PGV-6)

The same procedure was conducted to prepare PGV-6. Melting point 260–262° C. Yield=47%. NMR(DMSO-d6):

3.04(s, 4H, H$_2$C—CH$_2$); 7.32(s, 12H, —CH=); 7.68(s, 4H, arom); 10.81(br, 2H, —OH). HRMS (C$_{19}$H$_{12}$O$_3$Cl$_4$) obtained 427.9540; calculated 427.9541.

EXAMPLE 9

2,5-bis(4-hydroxy-3-methoxybenzylidene) cyclopentanone (PGV-0)

The same procedure was conducted to prepare PGV-0. Melting point 212–214° C. Yield=97%. NMR(DMSO-d6): 3.61(s, 4H, H$_2$C—CH$_2$); 4.51(s, 6H, —OCH$_3$); 7.42(d, 2H, J=8 Hz, H5); 7.7(d, 2H, J=8 Hz, H6); 7.75(s, 2H, H2); 7.83 (s, 2H—CH=); 8.79(s, 2H, —OH). HRMS (C$_{21}$H$_{20}$O$_5$) obtained 352,130; calculated 352,1311.

EXAMPLE 10

2,5-bis(4-hydroxy-3,5-dichlorophenyl)-1,4-pentadien-3-one (GVT-6)

The same procedure was conducted to prepare GVT-6. Melting point 255–256° C. Yield=56%. NMR(DMSO-d6): 7.28(d, 2H, —C=CH—CO—); 7.68(d, 2H, —CH=C—CO—); 7.86(s, 4H, arom); 10.82(br, 2H, —OH). HRMS (C$_{17}$H$_{10}$O$_3$Cl$_4$) obtained 401.9383; calculated 401.9384

Biological Activity and Toxicity of the Compounds of the Invention

EXAMPLE 11

Anti Inflammatory Activity Test

Carragenin was used as an inflammatory agent. The volume inhibition of rat paw edema following peroral administration of various doses of synthetic compounds in 1% CMC (Carboxy Methyl Cellulose) in comparison to that of control was used to determine the activity of the compounds. In order to evaluate the anti-inflammatory of each compound. Wistar rats (body weight ranging from 200–250 g) were used and divided randomly into 5 groups: one group served as control and 4 groups were treatment groups. The control group received the vehicle 1% CMC, while the treatment group received the synthetic compounds of the invention orally in 1% CMC. Doses of 10, 20, 40 and 80 mg/kg bw of each compound were given to the animals. One hour later, each animal received a subplantar injection of 0.05 ml of carragenin suspension in saline solution (NaCl 0,9%). The volumes of rat paw edema were measured immediately and every half an hour following the subplantar injection for 5 hours. Table 2 summarizes the results of this experiment.

TABLE 2

HEXAGAMAVUNONE (HGV)

| Molecule | R$_1$ | R$_2$ | R$_3$ | ED$_{50}$ (mg/kg. body weight) |
|---|---|---|---|---|
| HGV 1 | CH$_3$ | OH | CH$_3$ | 41 |
| HGV 2 | C$_2$H$_5$ | OH | C$_2$H$_5$ | 20 |
| HGV 6 | Cl | OH | Cl | 25 |

TABLE 2-continued

PENTAGAMAVUNONE (PGV)

| Molecule | R$_1$ | R$_2$ | R$_3$ | ED$_{50}$ (mg/kg. bodyweight) |
|---|---|---|---|---|
| PGV 1 | CH$_3$ | OH | CH$_3$ | 86 |
| PGV 2 | C$_2$H$_5$ | OH | C$_2$H$_5$ | 80 |
| PGV 5 | OCH$_3$ | OH | OCH$_3$ | 48 |
| PGV 6 | Cl | OH | Cl | 20 |
| PGV 0 | OCH$_3$ | OH | H | 25 |

GAMAVUTONE (GVT)

| Molecule | R$_1$ | R$_2$ | R$_3$ | ED$_{50}$ (mg/kg. body weight) |
|---|---|---|---|---|
| GVT 6 | Cl | OH | Cl | — |

EXAMPLE 12

Anti Bacterial and Anti Fungal Activity Test

Sterile medium of Bacto Muller Hinton was melted at 45°–50° C. and poured (25 ml) into a sterile Petrie dish (100 mm in diameter), and was left at room temperature for 1 hour.

The sterility was checked by overnight incubation (37° C.). The media was used immediately. Both gram positive and gram negative microorganisms were used. of The synthetic compounds were tested in 0.1, 0.2, and 0.4% DMSO solutions. Incubation was performed at 37° C. for 24 hours. The zones of inhibition induced by active compounds were measured in millimeters, and compared to DMSO, nipagin and curcumin on the growth of *E. Coli, S. pneumoniae, B. subtilis,* and *C. albicans*. Table 3 summarizes the results of this example.

TABLE 3

| | | Minimum Inhibition Concentration (%) | | |
|---|---|---|---|---|
| | Microorganism | HGV-6 | PGV-6 | GVT-6 |
| 1. | S. Aureus | 0.35 | 0.25 | 0.25 |
| 2. | S. pneumoniae | 0.05 | 0.10 | 0.05 |
| 3. | B. subtilis | 0.25 | 0.20 | 0.30 |
| 4. | C. albicans | 0.25 | 0.25 | 0.25 |

EXAMPLE 13

Inhibition of Lipid Peroxidation Activity Test

This procedure is based upon a literature method described by Haenen and Bast (*FEBS Letters*; 159(1–2)

:24–8 (1983)). Antioxidative activity (lipid peroxidation) was determined by measuring the reactive form of thiobarbituric acid (TBA), i.e., malondialdehyde.

The synthetic compounds (final concentration of 0.5, 1.0, 2.0, and 4.0 µM) and microsomes (final concentration 2 mg protein/ml) were incubated (37° C.; 5 minutes), in Tris-HCl/KCl (50 mM/150 mM, pH 7.4) with shaking (air being freely admitted). Ascorbic acid (0,5 ml, 200 µM) was neutralized with potassium hydroxide before addition to the reaction mixture. The reaction were started by adding freshly prepared ferrous sulfate solution (0,5 ml, 10 µM).

Lipid peroxidation was assayed by measuring adduct of malondialdehyde and thiobarbituric acid. An aliquot of the incubation mixture (0,3 ml) was stopped by mixing with ice cold-TBA-TCA-HCl-BHT solution (2 ml). After heating (15 min., 80° C.) and centrifugation (15 min.) the absorbance at 535 nm was determined. The TBA-TCA-HCl-BHT solution was prepared as described previously. After the addition of ascorbate (0.2 mM) and $Fe^{2+}$ (10 µM) to the incubation mixture aliquots were taken at 5 minutes and analyzed as described above. The results ($IC_{50}$'s) are summarized in Table 4 below:

TABLE 4

| Compound | $R_1$ | $R_2$ | $R_3$ | Antioxidative Activity ($IC_{50}$) |
|---|---|---|---|---|
| HGV-1 | $CH_3$ | OH | $CH_3$ | 2.46 µM |
| HGV-2 | $C_2H_5$ | OH | $C_2H_5$ | 1.97 µM |
| HGV-5 | $OCH_3$ | OH | $OCH_3$ | 1.70 µM |
| HGV-6 | Cl | OH | Cl | — |
| PGV-1 | $CH_3$ | OH | $CH_3$ | 2.20 µM |
| PGV-2 | $C_2H_5$ | OH | $C_2H_5$ | 2.21 µM |
| PGV-5 | $OCH_3$ | OH | $OCH_3$ | 0.99 µM |
| PGV-6 | Cl | OH | Cl | 14.89 µM |
| PGV-0 | $OCH_3$ | OH | H | 6.4 µM |
| GVT-6 | Cl | OH | Cl | — |

EXAMPLE 14

Acute Toxicity of Compounds in Rats and Rabbits

The toxicity of the compounds was tested in male and female Sprague-Dawley rats and rabbits.

The following compounds were administered at the listed dosages given in Table 5 below:

TABLE 5

| PGV-0 | Rats: 2.5; 3.55; 5.04; 7.13; 10.16 g/kg BW |
| | Rabbits: 0.13; 0.91 and 6.37 g/kg BW |
| HGV-1 | Rats: 2.55; 3.82; 5.73; 8.20 g/kg BW |
| | Rabbits: 0.0447; 1.745; 6.80 g/kg BW |
| PGV-1 | Rats: 1.82; 2.73; 4.1; 6.15 g/kg BW |
| | Rabbits: 0.213; 1.22; 6.90 g/kg BW |

For each trial, the toxicity was determined by observing the animals after administration of the compounds for symptoms of toxicity and death for 24 hours ($LD_{50}$). If the animals are not dead after 24 hours, the observations are continued for two weeks. The histopathology organs from the subjects are also studied.

None of the dosages lead to death of the subjects. The apparent $LD_{50}$ for HGV-1 when administered was 8.20 g/kg body weight for rats and 6.80 g/kg body weight for rabbits. The apparent $LD_{50}$ for PGV-1 was 6.15 g/kg body weight for rats and 6.90 g/kg body weight for rabbits. The apparent $LD_{50}$ for PGV-0 was 10.16 g/kg body weight for rats and 6.37 g/kg body weight for rabbits.

EXAMPLE 15

Ulcerogenicity Test

The ulcerogenicity of the compounds was tested in rats and rabbits. The dosages and the controls are given in Table 6 below:

TABLE 6

Rats:

1% tilose (negative control)
Diclofenac Na 4.5 mg/kg BW and Acetosal 45.25 mg/kg BW (positive control).
PGV-0: 20, 30, 40 and 50 mg/kg BW
HGV-1: 25, 50, 75 and 100 mg/kg BW
PGV-1: 20, 30, 40 and 50 mg/kg BW Rabbits:

1% tilose (negative control)
PGV-0: 40 and 80 mg/kg BW
HGV-1: 40 and 80 mg/kg BW
PGV-1: 80 and 160 mg/kg BW.

The responses to the doses were observed after a single dose and after multiple administrations (twice daily for 3.5 days).

Each dosage level of each compound was then assigned a score of ulcerogenicity. The score was determined by the length and diameter of ulcers and the amount of bleeding in gastrointestinal tract.

It was determined that HGV-1, PGV-1, and PGV-0 were relatively safe for the gastrointestinal tract and the duodenum at the tested dosages based on data from histopathological studies of the organs.

EXAMPLE 16

Subchronic Toxicity Test

The toxicity of the compounds was tested in male and female rats and rabbits.

The compounds were administered at the listed dosages once daily for ninety days, as shown in Table 7, below:

TABLE 7

Rats:

PGV-0: 27.6; 55.2; 110.4 mg/kg BW
PGV-1: 86.4; 172.8; 345.6 mg/kg BW
HGV-1: 40, 80, 160 mg/kg BW

Rabbits:

PGV-0: 13, 26 and 52 mg/kg BW

The animals were observed for toxicity symptoms and weighed daily to determine average daily weight gain. The food and drink intake of each animal at each dosage level was also recorded.

Pathology tests such as hematology, blood and urine chemical analysis were also conducted on each animal. In addition, histopathological changes in organs were recorded.

None of the subjects died during the ninety day trial. No toxic effects were noted for any of the compounds.

EXAMPLE 17

Glutathione S-Transferase Activity Test

GST activity towards dichloronitrobenzene (DCNB) was measured spectrophotometrically by the increment of absorbance at 345 nm due to 2-chloro-4-nitrophenyl S-glutathione (GS-CNB) formation from DCNB and glutathione (GSH) according to the methods of Habig et.al (1974). The reaction was done in a pair of cuvettes with a 1 cm light path and 1 ml inner volume, at room temperature (18–24° C.).

The reaction mixture contained 17.5 μl of liver cytosol (43.71 mg/ml of protein) of uninduced rats, 75 μl of GSH (50 mM in aquadest), 15 μl of varying concentration of DCNB (35 mM in ethanol) in a solution of phosphate buffer (0.1 M pH 7.5, final volume 750 μl). The control cuvette contained no enzyme solution and the difference in mixture volume was ignored. The reaction was started by adding a DCNB solution and the absorbance increase in the first 3 minutes was recorded (Both et.al, 1961).

In inhibition studies, 7.5 μl samples of curcumin and its derivatives in DMSO (of a certain concentration) were preincubated for 4 minutes before GSH and DCNB were added. The absorption differences (abs/min) were recorded on Milton Roy Spectrophotometer Genesys-5 (Simple kinetic program) at 345 nm (0–3 minutes). All assays were carried out in 4× replication (Meyer et al, 1995).

It was determined the HGV-1 had an inhibitory effect on GST activity with an $IC_{50}$ of 29.5 μM. PGV-0 also had an inhibitory effect on GST activity with an $IC_{50}$ of about 2.7 μM. PGV-2 had an inhibitory effect on GST activity with an $IC_{50}$ of about 43.5 μM.

Incorporation by Reference

The entire contents of all patents, published patent applications and other references cited herein are hereby expressly incorporated herein by reference Equivalents Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating a responsive state in a subject, comprising administering to a subject an effective amount of a compound of formula I such that said responsive state is treated, wherein said compound of formula I is:

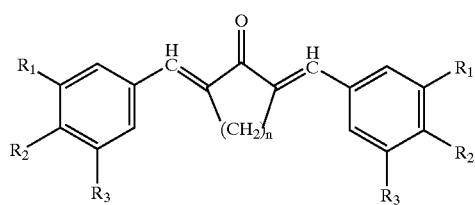

(I)

wherein n is an integer from 0 to 3, and $R_1$ and $R_2$ are each independently selected from the group consisting of methyl, ethyl, isopropyl, tertiary butyl, hydroxy, chloro, trifluoromethyl, methoxy, and dimethylamine; and $R_3$ is selected from the group consisting of methyl, ethyl, isopropyl, tertiary butyl, hydroxy, chloro, trifluoromethyl, methoxy, hydrogen, and dimethylamine; and pharmaceutically acceptable salts thereof.

2. The method of claim 1, wherein $R_3$ is selected from the group consisting of methyl, ethyl, isopropyl, tertiary butyl, hydroxy, chloro, trifluoromethyl, methoxy, and dimethylamine.

3. The method of claim 1 or 2, wherein said responsive state is an inflammatory disorder.

4. The method of claim 1, wherein said compound of formula I has an $ED_{50}$ value of 100 mg/kg body weight less.

5. The method of claim 4, wherein said compound of formula I has an $ED_{50}$ value of 50 mg/kg body weight or less.

6. The method of claim 5, wherein said compound of formula I has an $ED_{50}$ value of 40 mg/kg body weight or less.

7. The method of claim 6, wherein said compound of formula I has an $ED_{50}$ value of 30 mg/kg body weight or less.

8. The method of claim 3, wherein said inflammatory disorder is selected from the group consisting of osteoarthritis, rheumatoid arthritis, acute and chronic infections, bronchitis, sinusitis, upper respiratory infection, gastroenteritis, colitis, cystitis, urethritis, dermatitis, conjunctivitis, serositis, pericarditis, peritonitis, synovitis, pleuritis, tendinitis, uremic pericarditis, cholecystis, vaginitis, uveitis, drug reactions, insect bites, and burns.

9. The method of claim 1 or 2, wherein said responsive state is cancer.

10. The method of claim 1, wherein said responsive state is cancer and said compound is 2,5-bis(4-hydroxy-3-methoxybenzylidene)cyclopentanone, 2,5-bis(4-hydroxy-3,5-diethylbenzylidene)cyclopentanone, 2,6-bis(4-hydroxy-3,5-dimethylbenzylidene)cyclohexanone, or a pharmaceutically acceptable salt thereof.

11. The method of claim 9, further comprising administering a cytostatic agent.

12. The method of claim 9, wherein said cancer is selected from the group consisting of primary and metastatic solid tumors and carcinomas of the breast, colon, rectum, lung, oropharynx, hypopharynx, esophagus, stomach, pancreas, liver, gallbladder, bile ducts, small intestine, kidney, bladder, urothelium, cervix, uterus, ovaries, choriocarcinoma, gestational trophoblastic disease, prostate, seminal vesicles, testes, germ cell tumors, thyroid, adrenal, pituitary, hemangiomas, melanomas, sarcomas, Karposi's sarcoma, brain, nerves, eyes, astrocytomas, gliomas, glioblastomas, retinoblastomas, neuromas, neuroblastomas, Schwannomas, meningiomas, leukemia, chloroma, plasmacytoma, mycosis fungoides, cutaneous T-cell lymphomaeukemia, and lymphoma.

13. The method of claim 1 or 2, wherein said responsive state is a bacterial disorder.

14. The method of claim 13, wherein said bacteria disorder is associated with bacteria selected from the group consisting of S. Aureus, S. pneumoniae, B. subtilis, and C. albicans.

15. The method of claim 1 or 2, wherein said responsive state is a fungal disorder.

16. The method of claim 1 or 2, wherein said subject is immuno-compromised.

17. The method of claim 1 or 2, wherein said responsive state is an oxidative disorder.

18. The method of claim 17, wherein said compound has an $IC_{50}$ value of 5 μM or less.

19. The method of claim 18, wherein said compound has an $IC_{50}$ value of 4 μM or less.

20. The method of claim 19, wherein said compound has an $IC_{50}$ value of 3 μM or less.

21. The method of claim 20, wherein said compound has an $IC_{50}$ value of 2 μM or less.

22. The method of claim 21, wherein said compound has an $IC_{50}$ value of 1 μM or less.

23. The method of claim 1, wherein said subject is a mammal.

24. The method of claim 23, wherein said subject is a human.

25. The method of claim 1, wherein n is 3.

26. The method of claim 1, wherein n is 2.

27. The method of claim 25 or 26, wherein $R_2$ is hydroxy.

28. The method of claim 25 or 26, wherein at least one of $R_1$ and $R_3$ is methyl.

29. The method of claim 25, wherein said compound is 2,6-bis(4-hydroxy-3,5-dimethyl benzylidene) cyclohexanone.

30. The method of claim 26, wherein said compound is 2,5-bis(4-hydroxy-3,5-dimethyl benzylidene) cyclopentanone.

31. The method of claim 25 or 26, wherein at least one of $R_1$ and $R_3$ is ethyl.

32. The method of claim 25, wherein said compound is 2,6-bis(4-hydroxy-3,5-diethyl benzylidene)cyclohexanone.

33. The method of claim 26, wherein said compound is 2,5-bis(4-hydroxy-3,5-diethyl benzylidene)cyclopentanone.

34. The method of claim 25 or 26, wherein at least one of $R_1$ and $R_3$ is chloro.

35. The method of claim 25, wherein said compound is 2,6-bis(4-hydroxy-3,5-dichloro benzylidene) cyclohexanone.

36. The method of claim 26, wherein said compound is 2,5-bis(4-hydroxy-3,5-dichloro benzylidene) cyclopentanone.

37. The method of claim 25 or 26, wherein at least one of $R_1$ and $R_3$ is alkoxy.

38. The method of claim 25, wherein said compound is 2,6-bis(4-hydroxy-3,5-dimethoxy benzylidene) cyclohexanone.

39. The method of claim 26, wherein said compound is 2,5-bis(4-hydroxy-3,5-dimethoxy benzylidene) cyclopentanone.

40. The method of claim 1, wherein said compound is 2,5-bis(4-hydroxy-3-methoxy benzylidene) cyclopentanone.

41. The method of claim 1, wherein n is 0.

42. The method of claim 41, wherein $R_2$ is hydroxy.

43. The method of claim 41, wherein at least one of $R_1$ and $R_3$ is chloro.

44. The method of claim 42, wherein said compound is 2,5-bis(4-hydroxy-3,5-dichloro phenyl)-1,4-pentadien-3-one.

45. The method of claim 25, wherein $R_1$ and $R_3$ are not both methyl or methoxy.

46. The method of claim 25, wherein $R_3$ is methoxy and $R_1$ is not chloro.

47. The method of claim 25, wherein at least one of $R_1$, $R_2$ and $R_3$ is chloro, provided that when $R_1$ is chloro and $R_2$ is hydroxy, then $R_3$ is not methoxy.

48. The method of claim 1, wherein when n is 2 or 3, $R_1$ and $R_3$ are not both tertiary butyl.

49. A pharmaceutical composition comprising an effective amount of a compound of formula I:

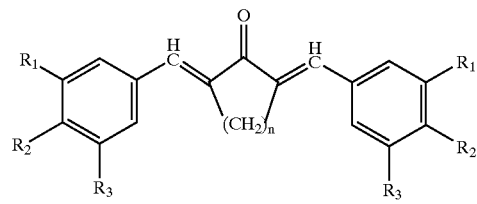

wherein
n is an integer from 0 to 3, and $R_1$ and $R_2$ are each independently selected from the group consisting of methyl, ethyl, isopropyl, tertiary butyl, hydroxy, chloro, trifluoromethyl, methoxy, and dimethylamine; and $R_3$ is selected from the group consisting of methyl, ethyl, isopropyl, tertiary butyl, hydroxy, chloro, trifluoromethyl, methoxy, hydrogen, and dimethylamine; and pharmaceutically acceptable salts thereof, and a pharmaceutically acceptable carrier.

50. The pharmaceutical composition of claim 49, wherein $R_3$ is selected from the group consisting of methyl, ethyl, isopropyl, tertiary butyl, hydroxy, chloro, trifluoromethyl, methoxy, and dimethylamine.

51. The pharmaceutical composition of claim 49, wherein said compound of formula I is selected from the group consisting of 2,6-bis(4-hydroxy-3,5-dimethyl benzylidene) cyclohexanone, 2,5-bis(4-hydroxy-3,5-dimethyl benzylidene)cyclopentanone, 2,6-bis(4-hydroxy-3,5-diethyl benzylidene)cyclohexanone, 2,5-bis(4-hydroxy-3,5-diethyl benzylidene)cyclopentanone, 2,6-bis(4-hydroxy-3,5-dichloro benzylidene)cyclohexanone, 2,5-bis(4-hydroxy-3,5-dichloro benzylidene)cyclopentanone, 2,5-bis(4-hydroxy-3,5-dimethoxy benzylidene)cyclopentanone, 2,5-bis(4-hydroxy-3-methoxy benzylidene)cyclopentanone, 2,6-bis(4-hydroxy-3,5-dimethoxy benzylidene)cyclohexanone, and 2,5-bis(4-hydroxy-3,5-dichloro phenyl)-1,4-pentadien-3-one.

52. The pharmaceutical composition of claim 49 or 50, wherein said effective amount is effective to treat an inflammatory disorder.

53. The pharmaceutical composition of claim 49 or 50, wherein said effective amount is effective to treat a bacterial disorder.

54. The pharmaceutical composition of claim 49 or 50, wherein said effective amount is effective to treat a fungal disorder.

55. The pharmaceutical composition of claim 49 or 50, wherein said effective amount is effective to treat an oxidative disorder.

56. The pharmaceutical composition of claim 49 or 50, wherein said effective amount is effective to treat cancer.

57. The pharmaceutical composition of claim 56, further comprising an effective amount of a cytostatic agent.

58. The pharmaceutical composition of claim 49 or 50, wherein said effective amount is not lethal.

59. A compound selected from the group consisting of 2,5-bis(4-hydroxy-3,5-dimethyl benzylidene) cyclopentanone, 2,5-bis(4-hydroxy-3-dimethoxy benzylidene) cyclopentanone, and pharmaceutically acceptable salts thereof.

* * * * *